United States Patent [19]

Robertson

[11] Patent Number: 4,555,368

[45] Date of Patent: Nov. 26, 1985

[54] PROCESS FOR SYNTHESIZING DIORGANOMONOTHIOPHOSPHINATES

[75] Inventor: Allan J. Robertson, Thorold, Canada

[73] Assignee: American Cyanamid Company, Stamford, Conn.

[21] Appl. No.: 675,492

[22] Filed: Nov. 28, 1984

[51] Int. Cl.$^4$ ................................................. C07F 9/30
[52] U.S. Cl. .......................... 260/502.4 R; 260/465 R; 260/465.1; 260/502.5 B
[58] Field of Search ..................... 260/502.4 R, 465 R, 260/465.1, 502.5 B

[56] References Cited

U.S. PATENT DOCUMENTS

| 3,232,830 | 2/1966 | Schrader et al. | 260/502.4 R |
| 3,238,248 | 3/1966 | Rauhut | 260/502.4 R |
| 3,261,857 | 7/1966 | Rauhut | 260/502.4 R |
| 3,812,223 | 5/1974 | Tsuchiya | 260/502.4 R |
| 3,833,662 | 9/1974 | Staendeke et al. | 260/502.4 R |
| 4,308,214 | 12/1981 | Robertson et al. | 260/502.4 R |

FOREIGN PATENT DOCUMENTS 1138771  10/1962  Fed. Rep. of Germany ... 260/502.4 R

OTHER PUBLICATIONS

Rauhut et al., "J. Am. Chem. Soc.", vol. 80 (1958), pp. 6690, 6691.

*Primary Examiner*—J. E. Evans
*Attorney, Agent, or Firm*—John W. Cornell

[57] ABSTRACT

A new and improved method for making diorganomonothiophosphinate compounds having the formula:

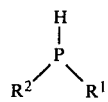

which comprises oxidizing a secondary phosphine in aqueous media to form the corresponding secondary phosphine oxide and reacting the secondary phosphine oxide thus formed with an excess of sulfur and an hydroxide compound at elevated temperature for a time sufficient until formation of the diorganomonothiophosphinate compound is substantially complete. The new and improved process of the present invention permits the preparation of diorganomonothiophosphinate. The products are stable in aqueous systems and are useful as sulfide collectors in froth flotation beneficiation of sulfide minerals.

10 Claims, No Drawings

PROCESS FOR SYNTHESIZING DIORGANOMONOTHIOPHOSPHINATES

BACKGROUND OF THE INVENTION

The present invention relates to a new and improved method for making diorganomonothiophosphinate compounds. More particularly, it relates to a process in aqueous media wherein a diorganophosphine is oxidized to form a diorganophosphine oxide, which is thereafter converted in the presence of sulfur and base to the corresponding diorganomonothiophosphinate compound.

Monothiophosphinate compounds are known to be useful as metal collectors for beneficiating certain mineral values from ores by froth flotation methods. The Soviet authors, P. M. Solozhenkin et al, in an article entitled, "Flotation Properties of Sulfur-Containing Phosphorus Derivatives." Dokl. Akad. Nauk Tadzh. SSR 13, No. 4, 26–30 (1970), for example, disclose that diethylmonothiophosphinic acid is a useful collector for galena, pyrite and antimonite. From the results of their study, they concluded that dithiophosphinate compounds performed better than monothiophosphinate compounds in flotations of these particular minerals.

More recently, it has been discovered, as is disclosed in commonly-assigned, copending application Ser. No. 675,489, filed Nov. 28, 1984, that diorganomonothiophosphinates provide exceptionally good metallurgical performance in selective flotation of base metal sulfide minerals, such as those of copper, nickel, molybdenum, cobalt and zinc, with selective rejection of pyrite, pyrrhotite and other gangue sulfide minerals, at reduced dosages over a broad range of pH values.

Prior art methods for making diorganomonothiophosphinate compounds are known. In one method, a corresponding diorganothiophosphoryl chloride is hydrolyzed to provide the corresponding diorganomonothiophosphinate, as summarized by the equation:

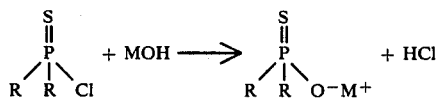

Another method for making diorganomonothiophosphinates is disclosed in the above-cited article by Solozhenkin et al, which comprises reacting phosphorus trichloride with primary alcohol to form dialkoxy substituted secondary phosphine oxide, followed by reaction with a Grignard Reagent, sulfur, and acidification to diorganomonothiophosphinic acid as summarized by the following reaction sequence:

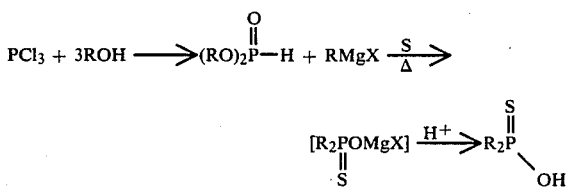

Still another method is disclosed in the article Hoffman, H. and P. Schellenbeck, "Dorstelling und Eigenschafter einiger Phosphorverlunding mit tert.-Butylgruppen". Chem. Ber. 99 1134 (1966). In accordance with this method, an alkyl or aryl-substituted phosphorus dichloride is reacted with a Grignard Reagent to form a secondary phosphorus chloride which is thereafter hydrolyzed to form the secondary phosphine oxide, or it is disclosed that a secondary phosphine may be oxidized directly with hydrogen peroxide to form the secondary phosphine oxide. The secondary phosphine oxide, in accordance with the disclosed process, may be sulfurized by adding sulfur to a solution of the secondary phosphine oxide in benzene and heating to form the corresponding diorganomonothiophosphinic acid solution in benzene. This method is summarized as follows:

$RPCl_2 + R^1MgCl \longrightarrow$

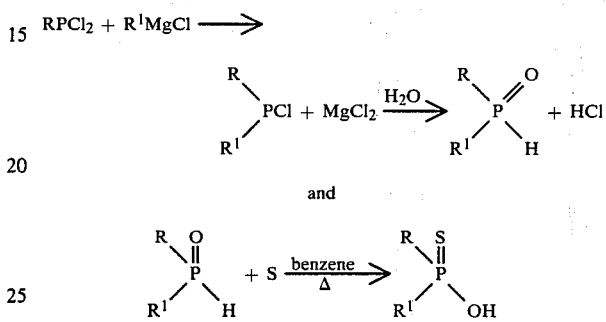

These prior art methods of making diorganomonothiophosphinate compounds have several shortcomings. The first two methods are not very economical for commercial production and therefore cannot be used to provide commercial quantities of diorganomonothiophosphinates for use as flotation reagents at a commercially acceptable price. Moreover, in the latter method of Hoffman et al, the need to use organic solvents, such as benzene, because of the instability of the diorganomonothiophosphinic acid products produced by the process in aqueous media, generally renders the method both economically and environmentally unattractive.

It is noteworthy that in an article published in J. Org. Chem 27, 2198 (1962), it is disclosed that a secondary phosphine sulfide cannot be oxidized to form a diorganomonothiophosphinate, i.e.,

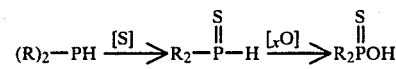

Accordingly, to overcome the disadvantages of the prior art methods, it is an object of the present invention to provide a new and improved method for making diorganomonothiophosphinate compounds in aqueous media in a commercially economical manner from readily available starting materials.

SUMMARY OF THE INVENTION

In accordance with this and other objects, the present invention provides a new and improved process for preparing diorganomonothiophosphinate compounds having the formula:

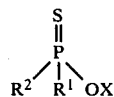

wherein $R^1$ and $R^2$ are each, independently, selected from saturated and unsaturated hydrocarbyl radicals, alkyl polyether radicals, and aromatic radicals; and such radicals optionally and independently substituted with polar groups selected from halogen, nitrile and nitro groups; or wherein $R^1$ and $R^2$ together form a heterocyclic ring having the formula:

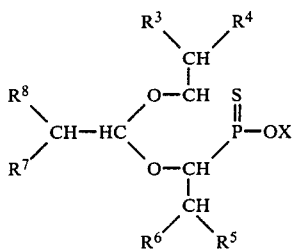

wherein $R^3$, $R^4$, $R^5$, $R^6$, $R^7$ and $R^8$ are each, independently, selected from hydrogen and $C_1$ to $C_{12}$ alkyl, and X is selected from hydrogen, alkali or alkaline earth metals and $NH_4$; said process comprising:

(a) providing a reactive mixture of at least one diorganophosphine compound of the formula:

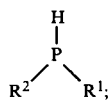

in an aqueous medium;

(b) gradually or incrementally adding an amount of an oxidizing agent sufficient to oxidize substantially all of the diorganophosphine in (a) to the corresponding diorganophosphine oxide,

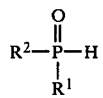

(c) heating the reactive mixture of step (b) to an elevated temperature and adding an excess amount of sulfur and an hydroxide compound selected from the group consisting of water, alkali metal or alkaline earth metal hydroxides and ammonium hydroxide; and (d) thereafter, permitting the reaction to proceed until formation of the diorganomonothiophosphinate compound is substantially complete.

In accordance with the present invention, a diorganophosphine is first oxidized to the corresponding diorganophosphine oxide by the addition of an oxidizing agent. The oxidation reaction is exothermic and for this reason, in order to control the temperature, the oxidizing agent is added slowly or in increments, such that the temperature of the reactive mixture is controlled at from about 40° to 60° C., preferably from about 50° to 55° C. The oxidizing agent is added in an amount sufficient to oxidize substantially all of the secondary phosphine to the corresponding secondary phosphine oxide, and generally an equimolar amount of oxidizing agent is used. Suitable oxidizing agents include, for example, air, oxygen, hydrogen peroxide, and hydrogen peroxide-liberating solids which give off $H_2O_2$ when introduced in an aqueous mixture, such as, alkali metal perborates, alkali metal carbonate peroxyhydrates and histidine perhydrate. Hydrogen peroxide is especially preferred because it is rapid, inexpensive and readily available.

After the secondary phosphine oxide has been obtained, it is reacted with an excess of sulfur and base to yield the diorganomonothiophosphinate. Generally, and without limitation, the sulfurization reaction is conducted at elevated temperatures on the order of from about 60° to 90° C., preferably from about 65° to about 75° C., for a time sufficient to provide the liquid diorganomonothiophosphinate product. Generally, the reaction mixture is heated for a period of from about 1 to about 7 hours, or until formation of the diorganomonothiophosphinate compound is substantially complete.

Remaining excess elemental sulfur can be readily removed from the reaction mixture by filtration. Depending on the concentration of the starting materials, the product obtained will vary from viscous oil to aqueous solution. In any form, the diorganomonothiophosphinate products are indicated by $^{31}P$ NMR spectra characterized by a —71 ppm shift with respect to phosphoric acid (85%), used as a reference. In concentrated form, the product is a viscous oil which will not recrystallize, so that a melting point is not readily determined. The product may be diluted to any desired concentration for use as a metal collector flotation reagent in the form of an aqueous solution, or it can be added in oil form.

The new and improved aqueous process of the present invention permits preparation of diorganomonothiophosphinate products in aqueous media and in a single reactor. The products of the process, because sulfurization is conducted in the presence of base, are stable in aqueous media for a substantial period. The starting materials are either commercially available or readily prepared from available materials.

Other objects and advantages of the present invention will become apparent from the following detailed description and illustrative working examples.

DETAILED DESCRIPTION OF THE INVENTION

In accordance with the new and improved process of the present invention, diorganomonothiophosphinate compounds are prepared from diorgano, i.e., secondary phosphines by first oxidizing the secondary phosphine in aqueous media in the presence of an oxidizing agent to provide a diorganophosphine oxide; and thereafter sulfurizing in the presence of a base at elevated temperature to provide a diorganomonothiophosphinate salt.

The secondary phosphines for use as starting materials in accordance with the process of the present invention, are generally represented by the formula:

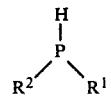

wherein $R^1$ and $R^2$ are the same as defined above. Several of the secondary phosphines, such as the dialkyl phosphines, are commercially available from a number of commercial suppliers. The secondary phosphines may also be made in accordance with well known methods, by reacting phosphine ($PH_3$) with a mono olefin in the presence of: strong bases as disclosed by M. M.

Rauhut et al in J. Am. Chem. Soc., 81, 1103 (1959); or by free radical initiation, e.g.

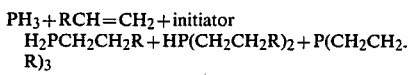

as disclosed in U.S. Pat. No. 2,803,597 and M. M. Rauhut et al, J. Org. Chem. 26, 5138 (1961), each of the above citations being specifically incorporated herein by reference. The secondary phosphines are easily separated from the primary and tertiary products by distillation. The addition reaction for making dialkyl, bis alkyl-, aryl alkyl- and bis- or di- aryl-substituted phosphines are presently very well known to those skilled in this art, and further details are amply provided in the above-cited references and elsewhere in the chemical literature.

For the particular embodiments, wherein $R^1$ and $R^2$ together form a heterocyclic ring, the secondary phosphine starting material will comprise a phosphine compound having the formula:

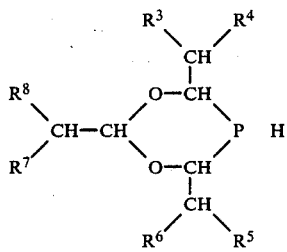

These heterocyclic secondary phosphines may be prepared by reacting phosphine ($PH_3$) with a corresponding alkyl or aryl aldehyde under acid catalyzed conditions.

More particularly, and with reference to certain preferred compounds for illustrative purposes, 1,3,5-triisopropyl-4,6-dioxa-2-phosphacyclohexane (TIP) compounds. e.g.

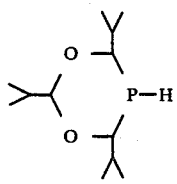

are prepared by reacting isobutyraldehyde and phosphine at a 3:1 molar ratio, respectively, using molar quantities of 100% phosphoric acid, as catalyst. The reaction is generally complete within 1 to 2 hours at 50° C. TIP product may be isolated by distillation. A 63% yield of TIP with negligible amounts of side products are obtained.

In accordance with the present process, the aqueous reaction mixture of the diorgano, or secondary, phosphine is carefully oxidized by addition of an oxidizing agent in an amount sufficient to oxidize substantially all of the diorganophosphine to form the corresponding diorganophosphine oxide. By careful oxidation is meant, that the oxidation reaction is performed by gradual or incremental addition of the oxidizing agent at a rate which provides a controlled temperature of from about 40° C. to 60° C., and preferably from about 50° to about 55° C. The amount of oxidizing agent added should be sufficient to oxidize substantially all of the secondary phosphine and generally an equimolar amount of oxidizing agent is used. The time of addition will vary depending on the starting amounts of secondary phosphine used. Generally, oxidation under controlled temperature conditions will be complete with gradual or incremental addition of the oxidizing agent over a period of from about 1 to about 3 hours.

Suitable oxidizing agents for use in the present process, as has been mentioned above, include oxygen, air, hydrogen peroxide, solids which liberate hydrogen peroxide such as alkali metal perborates, alkali metal carbonate peroxyhydrates and histidine perhydrate, as well as other peroxides and other oxidizing agents which will suggest themselves to those skilled in this art. The selection of a particular oxidizing agent is not critical, so long as it is effective to oxidize the secondary phosphine to the secondary phosphine oxide. Hydrogen peroxide is the preferred oxidizing agent for use herein, because it is inexpensive, readily available, and the temperature and rate of the oxidation reaction are easily controlled with its use.

After substantially all of the secondary phosphine has been converted to the corresponding secondary phosphine oxide, the aqueous reaction mixture is heated to an elevated temperature of between about 60° to about 90° C., and preferably from about 65° C. to about 75° C. Thereafter, an excess of sulfur and excess of an hydroxide compound are added to convert the secondary phosphine oxide to the corresponding diorganomonothiophosphinate compound. The aqueous sulfurization reaction in the presence of base is conducted at temperatures of between about 60° C. to 90° C., and allowed to proceed substantially to completion. Generally, the reaction is complete within a period of from about 1 to about 5 hours at temperatures of 60° C. to 90° C.

The process of the present invention provides quantitative yields of diorganomonothiophosphinate compounds. Any excess sulfur present in the aqueous reaction product mixture may be removed by filtration. Depending on the concentration of starting reactants, the products will be a viscous oil in more concentrated forms or an aqueous solution. The diorganomonothiophosphinate products are characterized by a $^{31}P$ NMR spectral shift at about $-71$ ppm with respect to phosphoric acid (85%), used as a reference.

The new and improved process of the present invention provides a simple two-step/one reactor method for making diorganomonothiophosphinate compounds in aqueous media which are stable in aqueous systems. The process of this invention provides a commercially-suitable method for making diorganomonothiophosphinates without the use of environmentally harmful organic solvents or expensive organometallic compounds.

Other objects and advantages of the present invention will become apparent from the following working examples which are provided by way of illustration only, to enable those skilled in this art to better understand and practice the present invention.

DETAILED DESCRIPTION OF PREFERRED EMBODIMENTS

PREPARATION 1

Synthesis of Heterocyclic Secondary Phosphine

The following reaction was performed in a phosphine autoclave reactor, and more particularly, in a one-gal- Ion stirred autoclave reactor equipped with internal and external heating/cooling coils, gas inlets and temperature and pressure gauges.

The autoclave was charged with 780 g (10.8 moles) of isobutyraldehyde and 333 g of 100% phosphoric acid. The autoclave lines were purged 3 times with nitrogen at 400 psig. A total of 116 g of phosphine ($PH_3$) was transferred to the autoclave and the mixture was stirred at 2000 rpm. Some cold water was passed through the internal cooling coil to promote the rate of phosphine take-up. The autoclave was heated to 50° C. using steam through the external heating system and the following temperature/pressure profile was observed:

| Time (min.) | Temp. (°C.) | Presence (Psig) | Remarks |
| --- | --- | --- | --- |
| 0 | 25 | 315 | Heat introduced |
| 15 | 70 | 276 | Some exotherm noted, External heat shut-off |
| 30 | 47 | 109 | External heat on |
| 45 | 51 | 86 | |
| 60 | 53 | 78 | |
| 75 | 52 | 67 | |
| 90 | 50 | 59 | Cooling Introduced |
| 95 | 25 | 50 | Phosphine Vented |

The autoclave was discharged under nitrogen into a 3-necked stainless steel flask. Total weight of the autoclave contents was 1170 grams.

The reaction product was transferred from the flask to a 2-liter separatory funnel under nitrogen and the brown spent acid lower layer weighing 405 g was separated. The top layer weighed 755 g. Analysis by $^{31}P$ NMR showed that the product contained high concentrations of 2,4,6-triisopropyl-1,3-dioxa-5-phospha cyclohexane (TIP) with very few side products.

A 171 g portion of this top material was distilled, first at atmospheric pressure to remove unreacted isobutyraldehyde (33 g) and second at 60°–61° C./0.4 mm to collect 118 g of product (63% yield).

A $^{31}P$ NMR spectrum of the distilled product showed three peaks at +70 ppm, +72 ppm and +112 ppm, against 85% phosphoric acid reference. Subsequent analysis by capillary GC-mass spectroscopy showed that the three components indicated by NMR were for the +112 ppm peak a noncyclic intermediate, and for the +72 ppm peak a tertiary phosphine impurity, and the +70 ppm peak corresponded to TIP. The spectral data were consistent with the TIP structure:

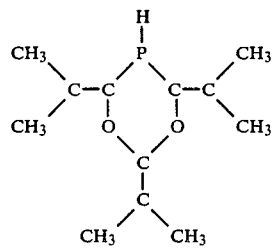

EXAMPLE 1

Preparation of Ammonium Diisobutyl Monothiophosphinate

In a stainless steel reactor were charged 570 grams of a diisobutyl phosphine, containing 95.5% of diisobutyl phosphine and 2.4% of triisobutyl phosphine impurity. 506 grams of a 24.29% $H_2O_2$ solution in water (1 mole) were added to the reactor over a period of 1 hour and 45 minutes, while controlling the temperature at 52°–53° C.

Thereafter, the temperature of the reaction mixture was raised to between about 68°–70° C. A mixture prepared by adding 308 grams of a 28% solution of aqueous ammonia to 125 grams of sulfur, was added to the reaction vessel and the temperature was maintained at 68°–70° C. for a period of 2½ hours. The reaction mixture was thereafter filtered to remove the excess sulfur. A quantitative yield of a viscous oil was obtained. $^{31}P$ NMR spectra of the oil product showed a —71 ppm shift with respect to 85% phosphoric acid used as a reference.

EXAMPLE 2

Preparation of Heterocyclic Secondary Phosphine Oxide 78 g of 2,4,6-triisopropyl-1,3-dioxa-5-phospha cyclohexane (TIP) prepared in Preparation 1 were dissolved in 250 mls of isopropyl alcohol and an air stream was passed through the solution at a rate which kept the temperature at between 40°–45° C., over a period of about 2½ hours. The solution was stoppered overnite. The following morning an airflow was again introduced to the solution and the flow was increased. The temperature was observed to go up to 40° C. and gradually went down to 20° C. over 2 hours at the same airflow.

The solution was stripped of isopropyl alcohol in a Rotovac to yield an oil. Some crystal formation occurred upon standing. The oily liquid seeded with crystals was dissolved in benzene and extracted two times with a dilute $NaHCO_3$ solution.

The organic layers were dried with $Na_2SO_4$, filtered and stripped on the Rotovac to yield 59.0 g of an oil.

The oil was seeded with crystals from earlier aliquots and let stand overnite. The following morning, the sample was solid. The solid was pressed on a clay plate. IR spectra was consistent with the structure for TIPO,

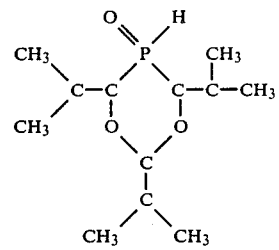

If the TIPO is diluted with water and reacted at a temperature of between 68°—70° C. with excess ammonium hydroxide and sulfur in accordance with the method of Example 1, then the corresponding ammonium 1,3,5-triisopropyl-4,6-dioxa-2-phospha cyclohexane monothiophosphinate will be obtained.

Although the present invention has been described with reference to certain preferred embodiments, modifications or changes may be made therein by those skilled in this art. Instead of diisobutyl phosphine, other secondary phosphines such as diisoamyl, di-sec-butyl, or diisopropyl phosphine may be employed as the starting material. Instead of ammonium hydroxide, sodium, lithium or potassium hydroxide may be employed in the sulfurization reaction. All such obvious modifications may be made herein by those skilled in this art without departing from the scope and spirit of the present invention as defined by the appended claims.

What is claimed is:

1. A method for making a diorganomonothiophosphinate compound of the formula:

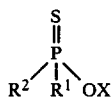

wherein R¹ and R² are each, independently, selected from saturated and unsaturated hydrocarbyl radicals, alkyl polyether radicals, and aromatic radicals; and such radicals optionally and independently substituted with polar groups selected from halogen, nitrile and nitro groups; or wherein R₁ and R₂ together form a heterocyclic ring having the formula:

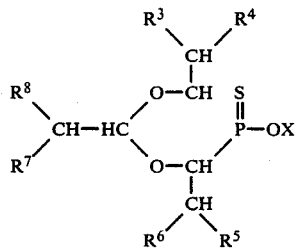

wherein $R^3$, $R^4$, $R^5$, $R^6$ $R^7$ and $R^8$ are each, independently, selected from hydrogen and $C_1$–$C_{12}$ alkyl; and X is selected from the group consisting of hydrogen, alkali or alkaline earth metals and $NH_4$; said process comprising:

(a) providing a reactive mixture of at least one diorganophosphine compound of the formula:

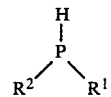

in an aqueous medium;

(b) oxidizing the diorganophosphine compound in (a) under controlled temperature conditions of between about 40° to about 60° C. by adding an amount of an oxidizing agent sufficient to oxidize substantially all of the diorganophosphine in (a) to the corresponding diorganophosphine oxide;

(c) heating the reactive mixture of step (b) to an elevated temperature and adding an excess amount of sulfur and an excess amount of an hydroxide compound selected from the group consisting of water, alkali metal or alkaline earth metal hydroxides and ammonium hydroxide; and (d) thereafter permitting the reaction to proceed until formation of the diorganomonothiophosphinate compound is substantially complete.

2. A method as recited in claim 1 wherein in step (c) the reactive mixture is heated to a temperature of between about 60° to about 90° C.

3. A method as recited in claim 1 wherein said oxidizing agent is selected from the group consisting of air, oxygen, hydrogen peroxide, and hydrogen peroxide-liberating solids.

4. A method as recited in claim 1 wherein said oxidizing agent is hydrogen peroxide.

5. A method as recited in claim 1 wherein R¹ and R² are each isobutyl.

6. A method as recited in claim 1 wherein R¹ and R² together form a heterocyclic ring and in said ring $R^3$, $R^4$, $R^5$, $R^6$, $R^7$ and $R^8$ are each methyl.

7. A method as recited in claim 1 wherein said hydroxide compound is ammonium hydroxide.

8. A method as recited in claim 1 wherein said oxidizing agent is added in an equimolar amount.

9. A method as recited in claim 1 wherein the diorganomonothiophosphinate compound formed is ammonium diisobutylmonothiophosphinate.

10. A method as recited in claim 1 wherein the diorganomonothiophosphinate compound formed is ammonium 1,3,5-triisopropyl-4,6-dioxa-2-phosphacyclohexane monothiophosphinate.

* * * * *

UNITED STATES PATENT AND TRADEMARK OFFICE
CERTIFICATE OF CORRECTION

PATENT NO.  : 4,555,368
DATED       : November 26, 1985
INVENTOR(S) : Allan James Robertson It is certified that error appears in the above-identified patent and that said Letters Patent is hereby corrected as shown below:

In The Abstract Delete:

" 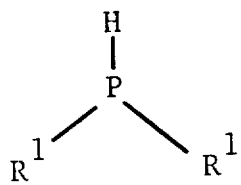 "    And Insert Therefor:

-- 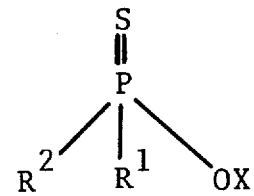 --

Signed and Sealed this

*Ninth* Day of *September 1986*

[SEAL]

*Attest:*

*Attesting Officer*

DONALD J. QUIGG

*Commissioner of Patents and Trademarks*